United States Patent [19]

Ohmi

[11] Patent Number: 5,428,990
[45] Date of Patent: Jul. 4, 1995

[54] METHOD OF EVALUATION SEGREGATION OF SOLID-LIQUID INTERFACE AND SEGREGATION APPARATUS THEREOF

[76] Inventor: Tadahiro Ohmi, 1-17-301, Komegabukuro 2-chome, Aoba-ku, Miyagi-ken, Sendai-shi 980, Japan

[21] Appl. No.: 150,129
[22] PCT Filed: May 13, 1992
[86] PCT No.: PCT/JP92/00608
 § 371 Date: Jan. 31, 1994
 § 102(e) Date: Jan. 31, 1994
[87] PCT Pub. No.: WO92/21954
 PCT Pub. Date: Dec. 10, 1992

[30] Foreign Application Priority Data

May 30, 1991 [JP] Japan .................... 3-155881

[51] Int. Cl.⁶ ............................................. G01N 13/00
[52] U.S. Cl. .................... 73/64.48; 73/53.06; 73/61.42; 73/61.71
[58] Field of Search ............. 73/64.48, 53.06, 60.11, 73/61.42, 61.43, 61.63, 61.71, 64.41, 64.48, 64.55

[56] References Cited

U.S. PATENT DOCUMENTS

3,661,564 5/1972 Gandon et al. .................. 75/101 R

FOREIGN PATENT DOCUMENTS

50-151480 12/1975 Japan .
63-210748 9/1988 Japan .

Primary Examiner—Hezron E. Williams
Assistant Examiner—J. David Wiggins
Attorney, Agent, or Firm—Young & Thompson

[57] ABSTRACT

A method and apparatus for evaluating a segregation at a solid-liquid interface, capable of specifying and measuring quantitatively a segregation substance, that is, a substance which precipitates preferentially on a solid surface from a liquid or remains preferentially in the liquid (or dissolves from the solid surface into the liquid), on the contrary. A reception table (2) having a shallow cup-like upper surface is disposed inside a container (1). After a predetermined inert gas is introduced into the container (1), a sample sheet (3) placed on the reception table (2) is downwardly curved by deformation means such as a vacuum suction mechanism. Thereafter, a predetermined solution is dropped onto the sample sheet (3) through a capillary (4) and the dropped solution is evaporated by a mercury lamp (7). After a predetermined amount of evaporation is completed, the sample sheet (3) is taken out from the container (1), and is analyzed by an appropriate one of measuring instruments attached to the apparatus. The particular instrument chosen for use in the apparatus depends on the nature of a segregation substance to be identified/quantified.

8 Claims, 5 Drawing Sheets

METHOD OF EVALUATION SEGREGATION OF SOLID-LIQUID INTERFACE AND SEGREGATION APPARATUS THEREOF

TECHNICAL FIELD

The present invention relates to a method for evaluating a segregation at a solid-liquid interface and an apparatus therefor, which is useful. In evaluating the type and amount of impurities adhering, for example, to a semiconductor substrate in a manufacturing process of a semiconductor device.

BACKGROUND ART

Conventionally, with respect to solid-liquid interfaces, in academic, the concept of a contact angle which was used to express the wettability of a liquid with respect to a solid surface was slightly known in the literature, and it can be said that almost no other evaluable research reports existed. On the other hand, in industry, since an increase in the cleanliness of a solid surface has been strongly desired in magnetic film technology for recording and in liquid crystal technology for flat screen displays, it can be said that a resolution of the solid-liquid interface problem will become progressively essential.

Hereinbelow, the solid-liquid interface problem will be discussed in the context of the most typical surface contamination and removal of surface contamination sources, using semiconductor technology as an example.

In semiconductors, there are three representative sources of surface contaminants: particles (hereinbelow, the term "particles" will include the so-called debris), metallic elements, and organic molecules. If the surface of a semiconductor is contaminated by any of these, the yield of acceptable products in semiconductor device production, and the reliability of the Finished products, decreases markedly. Accordingly, in semiconductor manufacturing processes, technology for the cleaning of semiconductor substrate surfaces has been developed, and chief among such technologies are wet washing technologies utilizing chemicals or ultra-pure water.

Here, in this wet washing technology, aqueous ammonium peroxide ($NH_4OH$—$H_2O_2$—$H_2O$) is used in the removal of particles or metallic elements from a semiconductor substrate surface, aqueous hydrochloric peroxide ($HCl$—$H_2O_2$—$H_2O$) is used in the removal of metallic elements, and furthermore, aqueous sulfuric peroxide ($H_2SO_4$—$H_2O_2$—$H_2O$) is used in the removal of primarily organic materials.

Then in the final stage of this wet cleaning, the thin natural oxide film which is formed on the substrate surface is removed using dilute hydrofluoric acid ($HF$—$H_2O$), and the chemicals and like remaining on the substrate surface are removed using ultra-pure water.

However, in this wet cleaning technology in semiconductor manufacturing, the quantized effects of the mutual interaction of ultra-pure water and chemicals (liquids) with the semiconductor (solid) surface were not known with respect to the problem of the ease of precipitation of, for example, impurities, such as particles or metallic elements, onto a solid surface, so that the effects of various types and amounts of impurities such as particles or metals or the like contained in a solution of ultra-pure water or chemicals (dilute hydrofluoric acid, aqueous hydrochloric peroxide, aqueous ammonium peroxide, aqueous sulfuric peroxide, and the like) on the cleanliness of a semiconductor surface, and the relationship between the semiconductor surface and the unavoidable contamination by these impurities, were not sufficiently clear.

In other words, it has not been made clear to what extent the cleanliness of the semiconductor is possible even if cleaning chemicals are initially employed. For this reason, at semiconductor manufacturing facilities, the management of chemicals, for example, the decision as to after what period to replace the chemicals has been conducted solely on the basis of trial and error, and this is unsatisfactory from the point of view of industrial productivity.

The present invention solves the problems present in the conventional technology described above; it has as an object thereof to provide a method and an apparatus for evaluating a segregation at a solid-liquid interface which is capable of specifying and measuring quantitatively a substance (hereinbelow referred to as a "segregation substance") which precipitates preferentially onto a solid surface from a solution of ultra-pure water or chemicals or the like, or which, on the contrary, remains preferentially in a solution of ultra-pure water or chemicals or the like (or which elutes into the liquid from the solid surface).

DISCLOSURE OF THE INVENTION

In order to attain the above object, the invention as disclosed in the preferred embodiment comprises: a first process, in which a sample sheet is supported within a container in an essentially horizontal state, a second process, in which an interior of the container is placed in an atmosphere which is inert at least with respect to this sample sheet, a third process, wherein the sample sheet is deformed so as to be downwardly curved a fourth process, wherein a predetermined solution is dropped onto a surface of the deformed sample sheet, a fifth process, wherein the dropped solution is heated and the solvent is allowed to evaporate for a predetermined period, and a sixth process, in which a solute remaining on the surface of the sample sheet as a result of evaporation is analyzed.

The apparatus corresponding to the inventive method above is a second preferred embodiment that comprises, in the case of the method disclosed in the preferred embodiment, a container capable of maintaining a hermetic state, a support mechanism for maintaining the sample sheet in an approximately horizontal state, disposed within the container, a deformation mechanism for deforming the supported sample sheet so as to curve downwardly, a solution supply mechanism for dropping a predetermined solution onto the supported sample sheet, a gas supply mechanism for introducing a gas which is inert with respect to the sample sheet into the container, and a heating mechanism for heating the solution on the sample sheet.

The invention disclosed according to a third preferred embodiment has a composition such that in the invention disclosed in the second preferred embodiment, the deformation mechanism comprises a vacuum suction mechanism for reducing the pressure of the atmosphere in approximately the central portion of the rear surface side of the supply sheet.

The invention disclosed in a fourth preferred embodiment has a composition such that, in the invention disclosed in the second preferred embodiment, the deformation mechanism comprises an electrostatic attraction mechanism which curves the central portion of the supply sheet downwardly by means of static electricity operating between the deformation mechanism and the supply sheet.

The invention disclosed in the fifth preferred embodiment has a composition such that, in the invention disclosed in one of the second preferred embodiment through the fourth preferred embodiment the gas comprises nitrogen gas.

The invention disclosed in the sixth preferred embodiment has a composition such that, in the invention disclosed in one of the second preferred embodiment through the fourth preferred embodiment, the gas supply mechanism is also capable of supplying another gas differing from the inert gas.

The invention disclosed in the seventh preferred embodiment has a composition such that, in the invention disclosed in one of the preferred embodiment through the sixth preferred embodiment, the other gas comprises oxygen gas.

The invention disclosed in the eighth preferred embodiment has a structured design composition such that, in the apparatus disclosed in one of the first seven preferred embodiments, the container has provided in the vicinity thereof apparatuses for analyzing the segregation substance on the sample sheet.

FUNCTION

A sample sheet (for example, a semiconductor substrate) is placed on a support mechanism (cup-like reception table) within a container in a roughly horizontal state (first process), and then the interior of the container is placed in an atmosphere of highly pure inert gas (nitrogen gas, argon gas, or the like) (second process).

Next, a deformation mechanism (a mechanism based on vacuum suction, electrostatic attraction, or the like) is engaged, and the sample sheet is bent so as to be downwardly curved within a range such that crystallographic flaws are not imparted (third process).

After this, a prespecified amount of a solution (organic solvents such as: ultra-pure water, dilute hydrofluoric acid, aqueous hydrochloric peroxide, aqueous ammonium peroxide, alcohol, or the like) containing, for example, particles (debris) or metallic impurities is dropped onto the sample sheet (fourth process).

Next, by the action of a heating mechanism, for example, a mercury lamp, a xenon lamp, an infrared lamp, or the like, the solvent of the solution on the sample sheet is evaporated (fifth process).

When the evaporation has been sufficiently conducted, the sample sheet is transferred to the outside of the container, and the segregation distribution is measured by means of a measuring apparatus, appropriate to the type of segregation substance remaining on the sample sheet, disposed in the vicinity of the container (sixth process).

A total reflection X-ray fluorescence meter (TRXRF) is typically used as the measuring instrument in the case in which the segregation substance comprises metallic elements, and a substrate surface particle counter is typically used as the measuring instrument when the segregation substance comprises particles (debris).

| Label Index of the Components in the Figures | |
|---|---|
| 1 | container, |
| 2 | reception table (support mechanism, deformation mechanism), |
| 3, 3A, 3B | semiconductor substrate (sample sheet), |
| 4 | capillaries (solution supply mechanism), |
| 7 | mercury lamp (heating mechanism). |

BEST MODE FOR CARRYING OUT THE INVENTION

Figure 1:
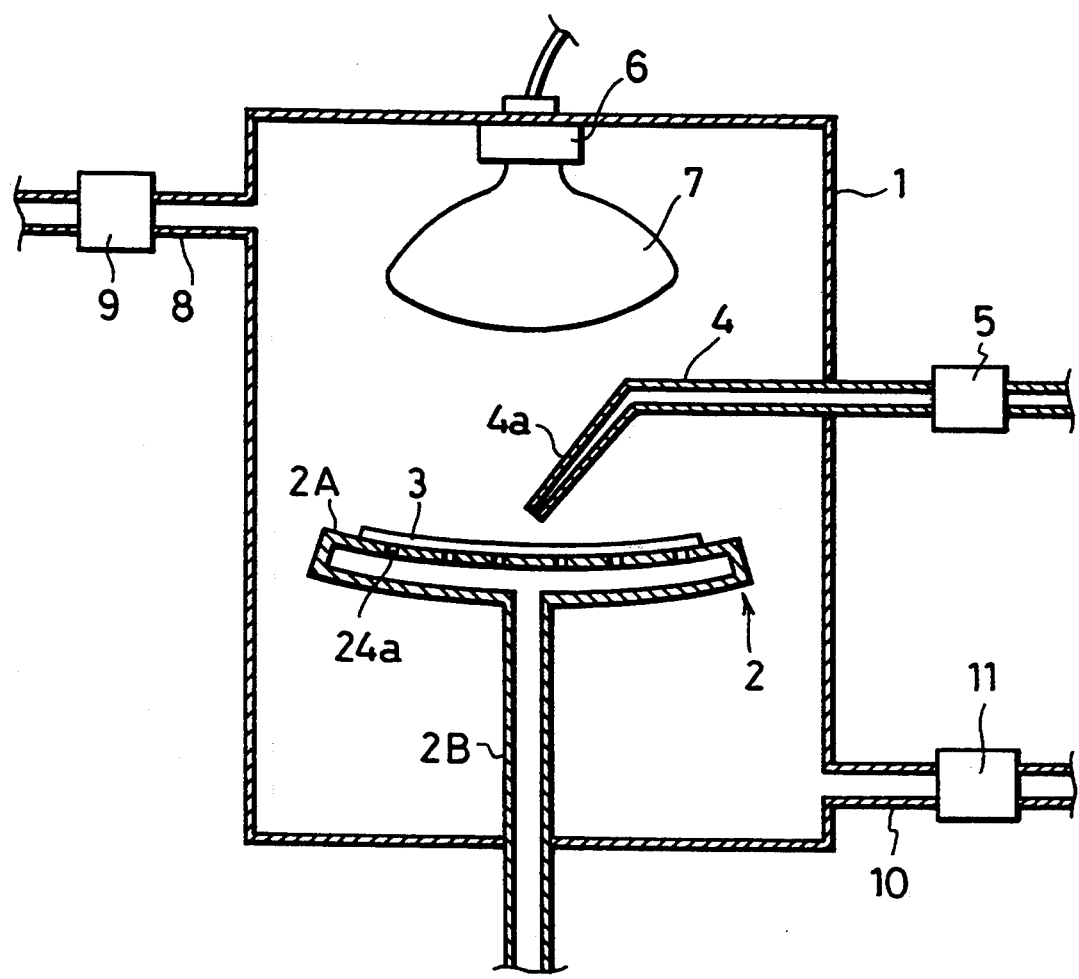
FIG. 1 is a cross-sectional view of the main parts showing an embodiment of a segregation apparatus in accordance with the present invention.

FIG. 1 shows an embodiment of a segregation apparatus in accordance with the present invention. As shown in the figure, in the container 1, which is hollow and is capable of maintaining a hermetic state, a reception table 2, which comprises the support mechanism, having formed thereon a shallow cup-like upper surface, is provided.

Reception table 2 comprises primarily reception surface portion 2A and support axle 2B; reception surface portion 2A and support axle 2B are hollow and communicate. In reception surface portion 2A, a plurality of suction holes 2Aa are formed, and support axle 2B penetrates the bottom surface portion of container 1 and is connected to a vacuum pump which is not depicted in the figure; suction holes 2Aa and a vacuum suction mechanism such as a vacuum pump or the like comprises the deformation mechanism. Semiconductor substrate 3 is placed on reception surface 2A.

Furthermore, a capillary 4 comprising the solution supply mechanism is provided at a position above reception table 2 in container 1, and a lead end portion 4a of capillary 4 is bent so that the opening thereof faces roughly the center portion of reception surface portion 2A. Capillary 4 extends through the side wall of container 1, and the end of this extending pipe is connected to a predetermined solution supply tank (not depicted in the diagram) through the medium of a liquid adjustment valve 5.

Furthermore, a socket 6 is attached to the upper surface of the interior of container 1, and a mercury lamp 7 (a xenon lamp is also acceptable) is installed in socket 6, and this is connected to an externally provided power source. This mercury lamp 6, or the like, comprises the heating mechanism. In this case, a structure is also possible in which this lamp is provided at the exterior of container 1, an irradiation window comprising a portion of container 1 comprising a transparent material such as silica glass or the like is provided, and the interior of container 1 is heated by means of the lamp provided externally via the irradiation window.

Furthermore, a gas input pipe 8 is provided in the upper side wall of container 1, and a nitrogen gas tank which is not depicted in the diagram is connected to the gas input pipe 8 through the medium of a gas valve 9, and a gas exhaust pipe 10 is provided in the lower side wall of container 1, and this gas exhaust pipe 10 is connected to an exhaust tank, which is not depicted in the diagram, through the medium of a gas valve 11.

In the vicinity of container 1, measuring instruments for analyzing the segregation substance on said semiconductor substrate 3 are provided. A total reflection X-ray florescence meter (TRXRF), a substrate surface particle counter, or the like, may be employed as such measuring instruments. The insertion and withdrawal of semiconductor substrate 3 is accomplished by means of a lid of container 1; this lid is not depicted in FIG. 1.

Next, an example of the use of the present embodiment, which is structured as described above, will be explained.

First, a semiconductor substrate 3 is placed in an essentially horizontal state on the reception table 2 within container 1, and the lid to container 1 is closed.

After this, the interior of container 1 is placed in an atmosphere of inert nitrogen gas of high purity.

Next, a vacuum pump which is coupled to reception table 2 is placed in operation, the rear surface side of semiconductor substrate 3 is placed under low pressure via suction holes 2Aa of reception surface portion 2A, and semiconductor substrate 3 is deformed so as to curve downwardly. In this case, the degree of curvature of semiconductor substrate 3 is established within a range such that flaws will not be imparted to the substrate 3.

After this, the degree of opening of liquid adjustment valve 5 is adjusted and a predetermined amount of a solution is dropped onto said semiconductor substrate 3. A solution is employed in which standard particles, for example, polystyrene latex (PSL) or silica latex (SiO$_2$L), comprising the soluent, are mixed in a solvent such as ammonia, an aqueous solution of ammonium peroxide, an aqueous solution of hydrochloric peroxide, a dilute solution of hydrofluoric acid, or the like; a solution may also be employed in which metallic element soluents, for example, iron (Fe), nickel (Ni), or copper (Cu), are mixed in a solvent such as ultra-pure water.

Figure 2:
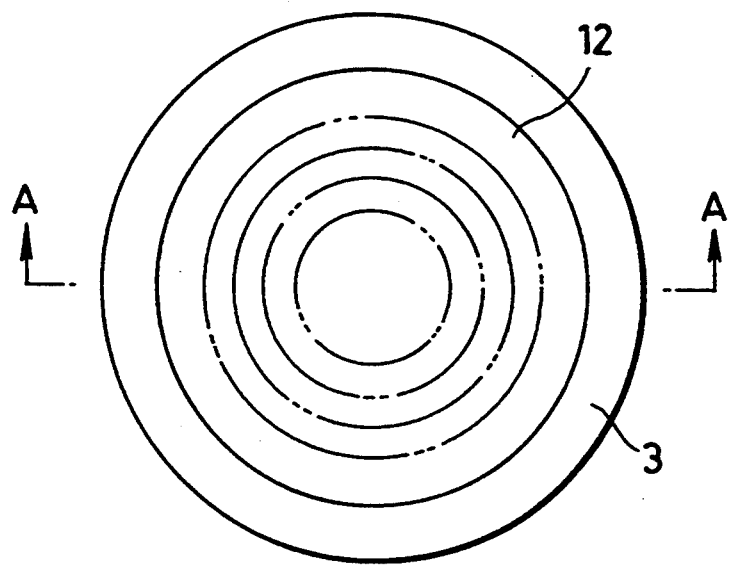
FIG. 2 is a top view showing the slate of the solution on the sample sheet which has been deformed.
Figure 3:
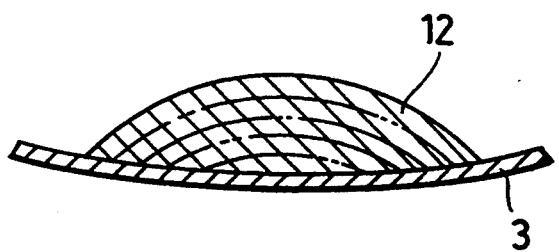
FIG. 3 is a cross-sectional view along the line A—A in FIG. 2.

Thereupon, the solvent of the solution on said semiconductor substrate 3 is evaporated by means of irradiation from mercury lamp 7. In this case, the process of the evaporation of the solution is as shown in FIG. 2 and FIG. 3. That is to say, the solution 12, which has pooled on substrate 3 so as to form a convex shape, has a outer diameter which becomes progressively smaller with the evaporation of the solvent. This change can be easily confirmed visually.

When the evaporation of solution 12 has been confirmed to have proceeded sufficiently, tire suction adhesion of semiconductor substrate 3 by means of the vacuum pump is halted, the lid of container 1 is lifted, and the semiconductor substrate 3 is removed from the container.

The remaining distribution of the segregation substance on semiconductor substrate 3 is measured by means of a measuring instrument which is in accordance with the type of segregation substance. A TRXRF is employed as tills measuring instrument in the case in which metallic elements are to be analyzed as the segregation substance, while a substrate surface particle counter is employed in the case in which particles are to be analyzed.

Figure 4:
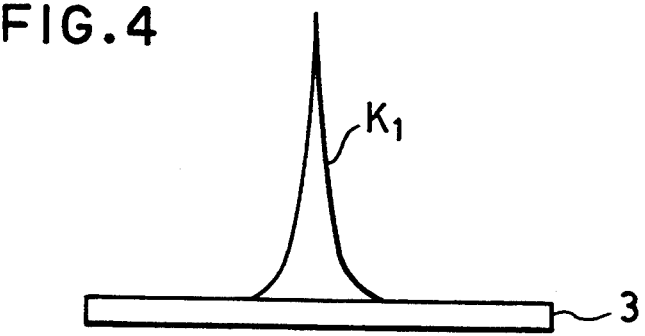
FIG. 4 is a type diagram showing an example of a distribution curve in the case in which an alkali solution is dropped onto the sample sheet.

FIG. 4 shows the results of the measurement by means of a particle counter of the distribution of the remaining substance on substrate 3 in the case in which a solution consisting of PSL mixed into aqueous ammonium peroxide was dropped. As can be understood from the curve $K_1$ in the figure, the remaining substance was concentrated in the center of substrate 3.

Figure 5:
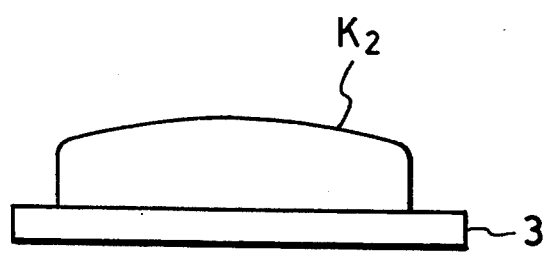
FIG. 5 is a type diagram showing an example of a distribution curve in the case in which an acidic solution is dropped onto the sample sheet.

FIG. 5 shows the results for the case in which a solution consisting of a mixture of PSL in aqueous hydrochloric peroxide was dropped. In this case, as can be seen from curve $K_2$, the segregation substance was distributed roughly equally over substrate 3.

Figure 6:
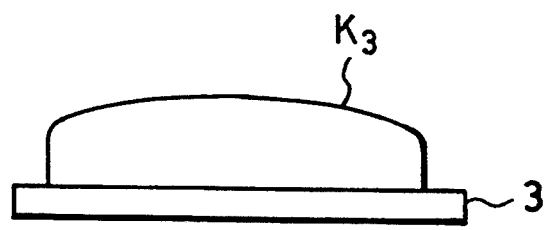
FIG. 6 is a type diagram similar to FIG. 5 for the case in which a different acidic solution is used.

FIG. 6 shows the results for the case in which a solution consisting of a mixture of PSL in dilute hydrofluoric acid was dropped. In tills ease, as earl be seen from curve $K_3$, the segregation substance was distributed roughly equally over substrate 3.

From the results shown in FIG. 4, above, it can be seen that the particles in the aqueous solution of ammonia, which is an alkali solution, tend to remain in the solution; they do not actively become attached to the semiconductor substrate surface. This indicates that an aqueous solution of ammonia may be employed in washing to remove particles adhering to a semiconductor surface.

From the results shown in FIG. 5 and FIG. 6 above, it can be seen that the particles present in aqueous solutions of hydrochloric peroxide or dilute hydrofluoric acid solutions, which are acidic solutions, are actively precipitated on the surface of semiconductor substrate 3.

In other words, while an alkali solution exhibits the effect of removing particles on a surface without segregating those particles on the surface of the semiconductor substrate 3, an acidic solution segregates the particles on the semiconductor substrate surface. That is to say, in the case in which an acidic solution is employed, it is necessary to completely remove the particles. In particular, in the Radio Corporation of America washing method, which is commonly known in the field of semiconductor substrate washing, in the case in which an acidic solution such as aqueous hydrochloric peroxide or dilute hydrofluoric acid or the like is employed after washing with aqueous ammonium peroxide, it is necessary to remove the particles from the acidic solution.

Figure 7:
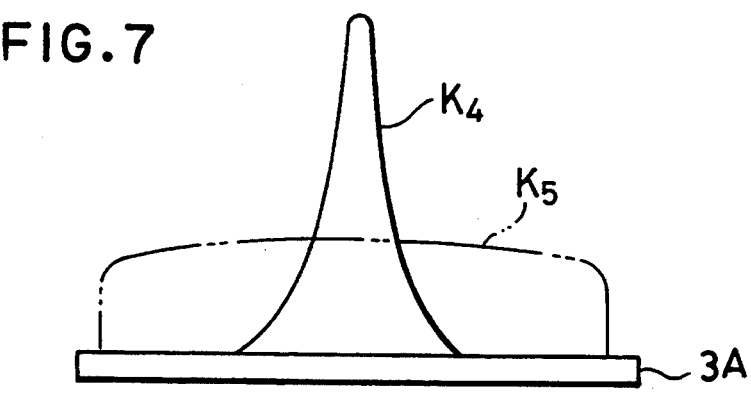
FIG. 7 is a type diagram showing the distribution curve of the segregation substance for the ease in which a solution of Fe, Ni, and Cu in ultra-pure water is dropped onto the semiconductor substrate and is then desiccated in an inert atmosphere.

Next, FIG. 7 shows the results of a case in which, after the interior of container 1 was placed in an atmosphere of highly pure nitrogen (N$_2$) gas, a solution of Fe, Ni, and Cu in ultra-pure water was dropped on the semiconductor (Si) substrate 3A, which was not covered with an oxide film; the analysis of the segregation substance was conducted by means of a TRXRF.

In FIG. 7, curve $K_4$ indicates the distribution of the remaining Fe; this distribution is such that the Fe is concentrated in approximately the center of substrate 3A. In contrast, curve $K_5$ indicates the distribution of the remaining Cu and Ni; and this distribution is such that the Cu and Ni are distributed approximately equally over the surface of substrate 3A.

The reason why the Fe remains in solution while the Cu and Ni are precipitated onto the substrate is thought to be that oxygen ($O_2$) is not contained in the atmosphere within container 1, and the surface of substrate 3A is not oxidized.

Figure 8:
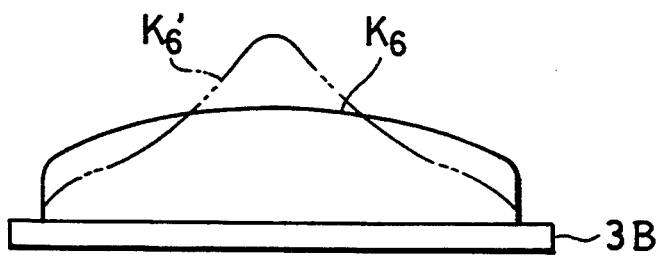
FIG. 8 is a type diagram showing the distribution curve of a segregated substance in the case in which a solution of Fe, Ni, and Cu in ultra-pure water is dropped onto a semiconductor substrate having formed on the surface thereof an oxide film, and this is desiccated in an atmosphere containing oxygen.

On the other hand, curve $K_6$ in FIG. 8 indicates the distribution of the remaining Cu in a case in which, after the interior of the container has been placed in an atmosphere in which approximately 20% $O_2$ has been added to desiccated $N_2$, a semiconductor substrate 3B which is not covered with an oxide film is placed on reception surface portion 2A, and a solution of Fe, Ni, and Cu in ultra-pure water is dropped onto this substrate 3B; the distribution is such that, as in the case of curve $K_5$ in FIG. 7, Cu is distributed approximately equally over the surface of substrate 3B.

In contrast, curve $K_6'$ indicates the distribution of the remaining Fe and Ni; this distribution is such that the Fe and Ni are concentrated approximately in the center of substrate 3B but also remain in the peripheral portions. That is to say, because the surface of substrate 3B is oxidized as a result of the oxygen present in the atmosphere, not merely Cu and Ni, but also Fe, is precipitated onto the surface of the substrate.

Figure 9:
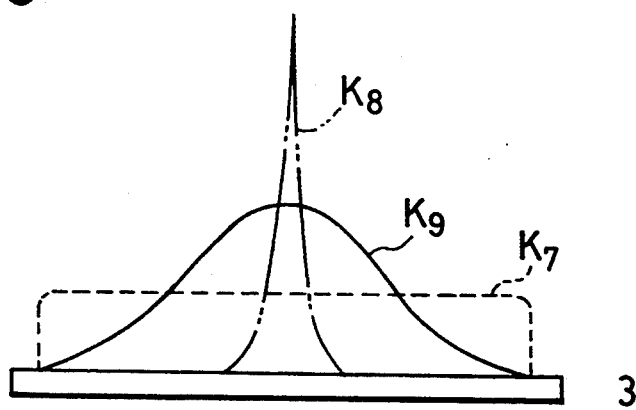
FIG. 9 is a type diagram showing the three distribution states of the segregation substance.

FIG. 9 shows in an overlapping fashion the tendencies in the remainder distribution of the segregation substances based on the above results.

First, the case of an equal distribution such as that shown by curve $K_7$ in FIG. 9 indicates a segregation substance (including both metallic elements and particles) which is easily precipitated from the solution onto the substrate. Next, the case of a centrally concentrated distribution such as that shown by curve $K_8$ in FIG. 9 indicates a tendency for the segregation substance to remain in solution. In addition, curve $K_9$ indicates a case in which the distribution is midway between that of curve $K_7$ and curve $K_8$, that is to say, a distribution in which the tendency for the segregation substance to remain in solution and the tendency for the segregation substance to be precipitated onto the substrate are approximately equal.

Figure 10:
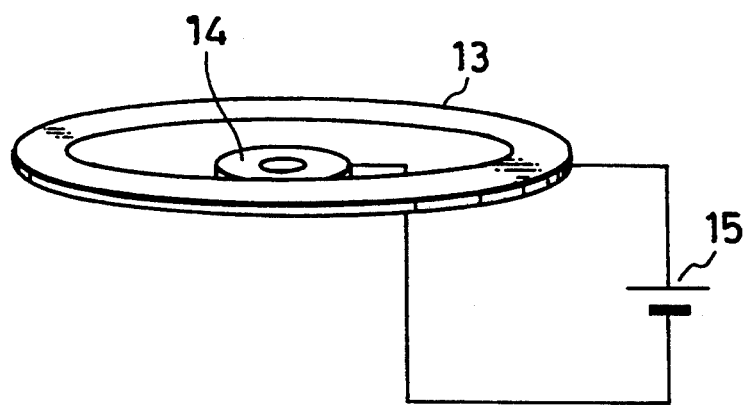
FIG. 10 is a perspective view showing an example of the structure of an electrostatic attraction mechanism.

In the above embodiment, composition was effected using a vacuum suction mechanism such as a vacuum pump or the like as the deformation mechanism; however, as shown in FIG. 10, the composition may also employ an electrostatic attraction mechanism. That is to say, first and second annular electrodes 13 and 14 are disposed in a concentric manner, and with respect to the outer first annular electrode 13, the inner second annular electrode 14 is disposed at a position slightly lower. In this case, the inner second annular electrode 14 forms an insulating film on the surface, and an electrostatic voltage power source 15 is applied between the electrodes 13 and 14.

By employing such a composition, an electrostatic current flows between the first electrode 13 and the second electrode 14, and the center portion of a sample sheet placed on the first electrode is drawn towards the second electrode 14, so that in the same manner as with the vacuum suction mechanism above, the sample sheet becomes downwardly curved.

INDUSTRIAL APPLICABILITY

The invention disclosed in the preferred embodiment comprises a first process, in which a sample sheet is supported in an approximately horizontal manner within a container, a second process, wherein the interior of this container is placed in an atmosphere which is inert at least with respect to the sample sheet, a third process, wherein the sample sheet is deformed so as to be downwardly curved, a fourth process, wherein a predetermined solution is dropped onto the surface of the deformed sample sheet, a fifth process, wherein the solution thus dropped is heated and the solvent is evaporated for a predetermined period, and a sixth process, wherein the substances remaining on the surface of the substrate after evaporation are analyzed, so that the precipitation, confirmation, and analysis of segregation substances becomes a simple matter, and it is possible to accurately investigate the solid-liquid interface problem, so that this will provide useful data, in particular in the field of semiconductor washing, and will contribute to an improvement in the manufacturing conditions of semiconductor production, and to an increase in the reliability of semiconductor products thru material purity.

The invention as disclosed in a first alternative embodiment is provided with a container, the inner atmosphere of which can be expelled, a support mechanism, which is disposed within this container and which supports the sample sheet in an approximately horizontal manner, a deformation mechanism which deforms the sample sheet which is thus supported so as to be downwardly curved, a solution supply mechanism, which drops a predetermined solution onto the surface of the sample sheet, a gas supply mechanism, which introduces a gas which is inert at least with respect to the sample sheet into the container, and a heating mechanism, which heats the solution on the surface of the sample sheet, so that it is possible to easily confirm the segregation phenomenon, and this invention is most appropriate for the execution of the process disclosed previously in the preferred embodiment. In the invention as disclosed in a second alternative embodiment the deformation mechanism comprises a vacuum suction mechanism which reduces the pressure of the atmosphere approximately in the central portion of the rear surface of the sample sheet, so that it is possible to easily conduct the deformation of the sample sheet by means of a simple mechanical composition.

In the invention as disclosed in the third alternative embodiment, the deformation mechanism comprises an electrostatic attraction mechanism which downwardly curves the central portion of the sample sheet by means of electrostatic force operating between the sample sheet and the electrostatic attraction mechanism, so that a deformation of the sample sheet can be easily realized by means of a simple electrical hardware-based structure.

In the invention as disclosed in a fourth alternative embodiment, in accordance with the invention as disclosed in one of the previous alternative embodiments, the gas comprises nitrogen gas, so that procurement is simple, and furthermore, this is effective in the case in which the segregation of only specified metallic elements such as Cu and Ni and the like is to be conducted.

In the invention as disclosed in a fifth alternative embodiment and a sixth alternative embodiment, the gas supply mechanism is capable of adding another gas which differs from the inert gas, so that this is effective for the case in which the segregation of other specified metallic elements such as Fe is to be conducted.

In the invention as disclosed in a seventh alternative embodiment, the container has a structural design composition with appropriate interconnections such that devices for the analysis of the segregation substances on the sample sheet are provided in the vicinity of the container, so that the analysis of the segregation substances can be conducted quickly and in an appropriate manner.

What is claimed is:

1. A method for evaluating segregation at a solid-liquid interface, comprising
    a first process, wherein a sample sheet is supported within a container in an approximately horizontal manner,
    a second process, wherein an interior of said container is placed in an atmosphere which is inert with respect to at least said sample sheet,
    a third process, wherein said sample sheet is deformed so as to be downwardly curved,
    a fourth process, wherein a predetermined solution is dropped onto the surface of said deformed sample sheet,
    a fifth process, wherein said dropped solution is heated and the solvent is allowed to evaporate for a predetermined period, and
    a sixth process, wherein a substance remaining on the surface of said sample sheet as a result of this evaporation is analyzed.

2. A segregation apparatus for evaluating segregation at a solid-liquid interface, comprising
    a container, an inner atmosphere of which can be exchanged,
    a support means for supporting a sample sheet in an approximately horizontal manner, disposed within said container,
    a deformation means for deforming said supported sample sheet so as to be downwardly curved,
    a solution supply means for dropping a predetermined solution onto the surface of said sample sheet,
    a gas supply means for introducing a gas which is inert at least with respect to said sample sheet into said container,
    a heating means for heating the solution on the surface of said sample sheet to evaporate the same, and
    means for analyzing a substance remaining on the surface of said sample sheet as a result of this evaporation.

3. A segregation apparatus in accordance with claim 2, wherein said deformation means comprises a vacuum suction mechanism which places the rear surface of said sample sheet, placed on a cup-like reception table, under reduced pressure.

4. A segregation apparatus in accordance with claim 2, wherein said deformation means comprises an electrostatic attraction mechanism which strongly acts, by means of electrostatic force, on the central portion of the rear surface said sample sheet, which is placed so that peripheral portions thereof are supported.

5. A segregation apparatus in accordance with claim 2, wherein said gas comprises nitrogen gas.

6. A segregation apparatus in accordance with claim 2, wherein said gas supply means is capable of adding another gas differing from said inert gas.

7. A segregation apparatus in accordance with claim 6, wherein said other gas comprises oxygen gas.

8. A segregation apparatus in accordance with claim 1, wherein said container has disposed in the vicinity thereof apparatuses for the analysis of segregation substances on said sample sheet.

* * * * *